United States Patent [19]

Holian et al.

[11] Patent Number: 4,745,077

[45] Date of Patent: May 17, 1988

[54] METHOD OF PERFORMING ASSAY FOR ANALYTE IN LIQUID MEDIUM

[75] Inventors: John Holian, Chalfont St. Giles; John C. Edwards, Great Missenden; John K. Martin, Wendover; Stephen A. Charles, Great Missenden, all of England

[73] Assignee: Amersham International plc., Buckinghamshire, England

[21] Appl. No.: 692,162

[22] Filed: Jan. 17, 1985

[30] Foreign Application Priority Data

Jan. 19, 1984 [GB] United Kingdom ............... 8401368

[51] Int. Cl.[4] ................ G01N 33/553; G01N 33/533
[52] U.S. Cl. .................... 436/526; 436/540; 436/544; 436/546; 436/800; 436/809; 252/62.51; 252/62.52; 252/62.54
[58] Field of Search ............. 436/526, 501, 540, 544, 436/546, 800, 809; 252/62.51, 62.52, 62.54

[56] References Cited

U.S. PATENT DOCUMENTS

| | | |
|---|---|---|
| 3,654,090 | 4/1972 | Schuurs et al. .................. 436/817 |
| 4,177,253 | 12/1979 | Davies et al. .................... 424/1 |
| 4,372,745 | 2/1983 | Mandle et al. .................. 436/537 |
| 4,415,700 | 11/1983 | Batz et al. ....................... 436/533 |
| 4,438,068 | 3/1984 | Forrest ............................ 422/61 |
| 4,554,088 | 11/1985 | Whitehead et al. ............. 252/62.54 |

*Primary Examiner*—Christine M. Nucker
*Attorney, Agent, or Firm*—Wenderoth, Lind & Ponack

[57] ABSTRACT

The invention concerns assays, such a immunoassays or two-site immunometric assays, performed using a labelled reagent and another reagent bound to magnetically attractable particles which are suspendable but insoluble in a liquid assay medium. After the labelled reagent has become partitioned between the liquid phase and the particles, in proportions which depend on the concentration of an analyte in a sample, the liquid phase is removed. Then the particles are re-suspended in another liquid medium, and the concentration of label observed. The method is particularly suitable for fluorescent and chemiluminescent' label systems, and can conveniently be performed in microtiter plates in which the wells are optically screened from one another, the observations being made from above or below the wells.

7 Claims, No Drawings

METHOD OF PERFORMING ASSAY FOR ANALYTE IN LIQUID MEDIUM

This invention is concerned with assays of the kind in which an analyte in a liquid medium is assayed by a method which involves partition of a labelled reagent between a liquid phase and a solid phase. Typically, the assay reagents include a solid phase reagent which may be particulate or in monolithic form e.g. as a coating on an assay tube, and a labelled reagent initially in the liquid phase. Assays of this kind are very well known and include immunoassays and immunometric assays.

In most assays, after incubation of the reagents, the solid phase is separated from the liquid phase, and a measurement is made of the amount of label in either the solid phase or the liquid phase. When a particulate solid is used, separation of the two phases has generally been effected by settling (slow) or by centrifuging (fairly quick but difficult to automate). More recently magnetically attractable particles which are suspendable but insoluble in the liquid phase have been used as reagent carriers; these have the advantage that they can quickly be separated from the liquid phase by the use of magnets and without the need for centrifuging.

European Patent Specification No. 30086A describes a test-tube assembly for use in assays utilizing magnetically attractable particles, which comprises a plurality of test-tubes mounted in a planar support member, and a planar base member comprising magnets, wherein the support member can be releasably coupled to the base member in such a way that the magnets attract and retain magnetically attractable particles in the tubes, the assembly being invertable to decant liquid from the tubes while retaining magnetically attractable particles therein.

In one embodiment, an assay involves the use of a radioactively labelled reagent initially in the liquid phase and another reagent bound to suspendable magnetically attractable particles. The reagents are incubated with samples containing the analyte in test-tubes in the support member. This is then coupled to the base member so as to bring down the particles. The assembly is inverted to remove the supernatant liquid. The particles in the tubes are washed and the supernatant liquid again removed. Finally, the radioactivity in each tube is measured by inserting the test-tubes in the support member in a multi-head counter.

While this embodiment is in many ways convenient, it does suffer from the disadvantage that a radioactively labelled reagent is used. Handling radioactivity requires special precautions and equipment which are not always readily available in laboratories that might otherwise perform the assay. Also, multi-head counters of radioactivity are rather large and cumbersome items of equipment, due to the need to shield each counting head from radiation from neighboring counting wells.

The European Patent Specification does contemplate the use of non-radioactive optical e.g. fluorescent labels. But the only technique described involves precipitating the magnetic particles and then observing optical properties e.g. fluorescence in the resulting supernatant liquid. Such observation is necessarily made from the side of the assay vessel, in order that the precipitate be screened from observation. Multi-head equipment for this purpose is not currently available, and would in any case be expensive and cumbersome. No practicable assay system using an optical label is described.

The present invention results from our discovery that, when magnetically attractable particles carrying a bound labelled reagentt which can emit or generate a fluorescent or luminescent signal are re-suspended in a liquid medium, it is possible to observe the signal generated by the labelled reagent in the suspension. Furthermore, the strength of the signal bears a definite relationship to the concentration of the labelled reagent. This discovery is surprising, since magnetically attractable particles, unlike conventional solid particles of e.g. polyacrylamide, are necessarily opaque. It would have bee reasonable to expect that, as a result of the opaque particles, little or no observable signal would be generated by the labelled reagent in the suspension.

This surprising discovery has an important practical consequence. It becomes possible to use a fixed array of assay vessels for performing an assay involving fluorescent or luminescent signals. The signal can be observed from above or below, and no radiation shielding is required, so the assay vessels can be made very small and positioned very close together. In fact, microtiter plates can be used.

The present invention provides a method of performing an assay of an analyte in a liquid medium, comprising the use of:
(i) individual assay vessels or an array of assay vessels in fixed relationship to one another,
(ii) a labelled reagent for the assay which is soluble in the liquid medium, and
(iii) another reagent for the assay bound to magnetically attractable particles which are suspendable but insoluble in the liquid medium
which method comprises
(a) incubating in the assay vessels a sample containing the analyte with the other reagents for the assay whereby the labelled reagent becomes partitioned between the liquid phase and the magnetically attractable particles in proportions which depend on the concentration of the analyte in the sample,
(b) separating the liquid phase from the magnetically attractable particles, and removing the liquid phase from the assay vessels,
(c) resuspending the magnetically attractable particles in another liquid medium and observing a signal generated by the labelled reagent thereon.

The method of this invention preferably uses an array of assay vessels in fixed relationship to one another. Use of such an array has practical advantages of ease and speed of handling, which are important where large numbers of repetitive actions have to be carried out. Handling of individual assay vessels is eliminated. Automatic dispensing of different reagents is facilitated. Confusion between assay vessels, which is inevitable when vessels are handled individually, is practically avoided.

The array of assay vessels is preferably planar with individual assay vessels arranged regularly in rows and columns. As mentioned above, microtiter plates may be used with adavantage. Commercially available microtiter plates are of injection molded plastic containing 96 wells each of approximately 0.3 ml capacity, arranged in 8 rows of 12. Both clear and opaque (white or black) plates are available.

Microtiter plates are widely used in microbiology, and have been used to a small extent for performing assays of the kind with which this invention is concerned. But such use has been limited by the problems of separating a solid reagent from the liquid phase. While it is possible in principle to coat the sides of each well with a solid phase reagent, it has proved difficult in practice to introduce the same amount of solid phase reagent into each well; and for a precise assay, it is necessary that the amount of each reagent in each tube be accurately the same. This difficulty; which has not been overcome, may arise from the molding technique used to make the plate; some wells are inherently more receptive to reagent than others.

If a particulate solid phase reagent is used, then two problems arise. Centrifuging microtiter plates is inconvenient. Also, a pellet of solid material results from bringing down a particulate reagent out of suspension, and it is difficult to make useful measurements of any optical signal generated from the pellet. The present invention overcomes all these problems, by using magnetically attractable particles which are re-suspended in liquid prior to observing the signal, and permits the widespread use of microtiter plates for immunoassays.

The method of this invention involves the use of a labelled reagent which is initially in the liquid phase but which becomes partitioned between liquid and solid phases. While the nature of the label is not critical, the method is particularly well suited for fluorescent and luminescent systems. The label is therefore preferably a group which, when suitably treated, gives rise to a fluorescent or luminescent signal. Fluorescent and luminescent systems are well known in the art and do not in themselves form part of this invention. One known chemiluminescent system involves a peroxidase enzyme with a luminol-type substrate. One known fluorescent system involves an alkaline phosphatase enzyme with a methylumbelliferone phosphate substrate. When the signal system is made up of several components, it will be understood that any one of the components may constitute the label of the labelled reagent.

The term "labelled reagent" includes reagents that are labelled after incubation with the assay sample. Similarly, the term "reagent bound to magnetically attractable paticles" includes reagents that are so bound after incubation with the assay sample. Assay techniques of this kind are known, and some are discussed below.

Several requirements attach to the magnetically attractable particles used in the method. These particles must carry a reagent which can bind another reagent initially present in the liquid phase. The particles must be suspendable in the liquid phase, preferably without shaking, for a period at least as long as the incubation time of the assay. This requirement suggests particles of small size and density approximating to that of the liquid phase. On the other hand, the particles must be magnetically attractable, preferably to an extent to permit quick and easy separation by magnets from the liquid phase. This requirement suggests a high proportion of ferromagnetic material, necessarily of rather high density. These conflicting requirements have proved somewhat difficult to meet, but there are now commercially available particles of micron size comprising powdered ion oxide or magnetite embedded in a plastics matrix, and having a specific gravity of 1.15 to 1.2.

The exact nature of the magnetically attractable particles used is not critical to this invention. It is, however, desirable that the particles carry a high concentration of the chosen reagent. If the reagent concentration on the particles is too low, then the concentration of labelled reagent that becomes bound to the particles during the course of the assay will necessarily be low. Because part of the signal generated by the label is inevitably obscured by the particles, the level of signal generated needs to be rather high. It is surprising that the concentration of the reagent that can be attached to the particles is sufficiently high to enable a useful signal to be generated in the assay. As a rule of thumb, the magnetically attractable particles should not attenuate the signal generated by the labelled reagent thereon by more than about 90%, preferably by no more than 50%.

Various assays have been described in the literature in which a labelled reagent becomes partitioned between a liquid phase and a solid phase. These involve reaction between the analyte and a specific binder for the analyte. Typical analyte/specific binder combinations include antigen/antibody, hapten/antibody and antibody/antigen. One class of assay to which this invention is particularly applicable is known as competition assay or immunoassay. In this class, the labelled reagent is the analyte or a derivative thereof coupled to a signal generating group. The specific binder is bound to the magnetically attractable particles, either before, during, or after the incubation with the assay sample. In the assay, the analyte in the assay sample and the labelled analyte derivative compete for reaction with a known amount of the solid phase specific binder. The proportion of the labelled analyte derivative that becomes bound to the solid phase is a measure of the concentration of the analyte in the sample. In this assay, it is important that the amount of solid phase specific binder be constant from one assay vessel to the next, and the use of magnetically attractable particles as carriers makes this easy to achieve.

In another assay, a 2-site immunometric assay, the assay sample is incubated with excess antibody, which is either in the solid phase throughout or is insolubilized during or after incubation, whereby the analyte in the sample becomes bound to the solid phase. A labelled antibody to the analyte, or an antibody to the analyte followed by a labelled reagent for binding to the said antibody, is added to the liquid phase, and the amount of the label that becomes bound (through the analyte) to the solid phase is directly proportional to the concentration of analyte in the assay sample.

The nature of the analyte is not critical. The invention is of use in relation to all liquid phase analytes that can be assayed by a technique which involves partition of a labelled reagent between a liquid and a solid phase. The method involves incubating the reagents, either all together or in sequence, for a time in accordance with conventional assays for the analyte. After incubation, the solid phase is brought down out of suspension and the supernatant liquid removed. The solid phase may be washed and is then re-suspended in a fluid medium prior to observing a signal generated by the labelled reagent. When a microtiter plate is used, the sequence of steps may typically be as follows:

A. Dispense samples, standard, labelled reagent, magnetically attractable particles carrying solid phase reagent, and any other desired reagents to the various wells of the plate.

B. Maintain the plate at a desired temperature for a time to incubate the reaction mixtures in the wells.

C. Place the plate on a planar magnet system for a time to bring the magnetically attractable particles down out of suspension.

D. Invert the plate/magnet assembly to decant the supernatant liquid, or remove the liquid by aspiration.

E. Remove the magnet system and add a wash buffer to re-suspend the particles.

F. Again bring down the particles by use of the magnet system and remove the supernatant liquid.

G. Remove the magnet system and add a liquid to re-suspend the particles, the liquid containing any further reagents required to react with the labelled reagent to generate a signal.

H. Observe, after incubation if necessary, the signal generated in each well of the microtiter plate.

For measuring fluorescence or chemiluminescence, it is necessary that each well be optically screened from its neighbors. Equipment is commercially available for measuring fluorescence in the individual wells of standard opaque black microtiter plates. Depending on the chemical system used, a chemiluminescent signal may be emitted either as a short-lived "flash" of light or as a substantially constant light emission.

The following Examples illustrate dthe invention.

EXAMPLE 1

Immunoassay of total thyroxine using chemiluminescence

1. The following reagents were incubated together in the wells of a white microtiter plate (Dynatech Laboratories Ltd., Billingshurst) for 60 minutes at 37° C.:
    25 microliters of a standard solution of thyroxine in human serum.
    125 LL microliters of a solution of thyroxine coupled to horse radish peroxidase in a Tris buffer, pH 8.3, containing a binding protein blocking agent.
    125 microliters of a suspension of magnetizable latex particles coated with sheep anti-thyroxine serum in 10 mM phosphate buffer, pH 7.6 (containing approximately 0.15 mg particles).

2. After the incubation, the magnetizable particles were settled by placing the microtiter plate over a magnetic plate containing an array of ferrite magnets.

3. The supernatant liquids were decanted from the wells of the microtiter plate by inversion while maintaining contact between the magnetic plate and the microtiter plate.

4. The particles in each well were then washed by resuspending in 200 microliters of 0.1M Tris buffer, pH 8.0, settling the particles on the magnetic plate, and decanting off the supernatant liquids.

5. The particles in each well were then resuspended in 200 microliters of a reagent for the chemiluminescent detection of peroxidase bound to the magnetizable particles, containing 25 mg/l luminol, 160 mg/l sodium perborate and 20 mg/l of an enhancer as described in European Patent Specification No. 87959A in 0.1M Tris buffer, pH 8.0.

6. After approximately one minute, the microtiter plate was placed in an instrument to measure the light emitted from each well.

| Thyroxine Standard (micrograms/100 ml) | Luminescence units | |
| --- | --- | --- |
| 0 | 1955, | 1916 |
| 2.3 | 1262, | 1246 |
| 5.6 | 680, | 676 |
| 11.7 | 354, | 334 |
| 22.7 | 187, | 172 |

EXAMPLE 2

Immunoassay of free thyroxine using chemiluminescence

1. The following reagents were incubated together in the wells of a white microtiter plate for 60 minutes at 37° C.:
    25 microliters of a standard solution of free thyroxine in human serum.
    125 microliters of a solution of a suitable conjugate of thyroxine with horse radish peroxidase in 50 mM phosphate buffer, pH 7.4, containing 0.9% sodium chloride and 0.1% fatty acid-free bovine serum albumin.
    125 microliters of a suspension of magnetizable latex particles coated with sheep anti-thyroxine serum in 10 mM phosphate buffer, pH 7.6 (containing approximately 0.25 mg particles).

2. After the incubation, the particles were washed, and resuspended in reagent for the chemiluminescent measurement of peroxidase as described in Example 1. The light emitted from each well was then determined after about one minute.

| Free Thyroxine Standard (ng/100 ml) | Luminescence Units | |
| --- | --- | --- |
| 0 | 3550, | 3440 |
| 0.2 | 3285, | 3347 |
| 0.51 | 2940, | 2844 |
| 1.0 | 2465, | 2449 |
| 1.97 | 1533, | 1617 |
| 4.79 | 656 | 690 |
| 9.5 | 424, | 137 |

EXAMPLE 3

Immunoassay of unconjugated oestriol using chemiluminescence

1. The following reagents were incubated together in a series of 55 mm × mm test tubes for 30 minutes at room temperature:
    25 microliters of a standard solution of unconjugated oestriol in human serum.
    100 microliters of a solution of oestriol coupled to horse radish peroxidase in 50 mM phosphate buffer, pH 7.4, containing 0.9% sodium chloride and 0.1% fatty acid-free bovine serum albumin.
    500 microliters of a suspension of magnetizable latex particles coated with rabbit anti-oestriol serum in 10 mM phosphate buffer 7.6 (containing approximately 0.6 mg particles).

2. After the incubation, the magnetizable particles were settled by placing the tubes over an array of ferrite magnets and the supernatant liquids were removed.

3. The particles in each tube were then washed by resuspending in 1.0 ml of 0.1M Tris buffer, pH 8.0, settling the particles on the magnets and removing the supernatant liquids.

4. The particles in each tube were then resuspended in 1.0 ml of a reagent for the chemiluminescent measurement of peroxidase as described in Example 1. After about 10 minutes the light emitted from each tube was determined using a luminometer (Lumac BV, Holland) with an integration time of 10 seconds.

| Oestriol Standard (ng/ml) | Photon Counts in 10 Seconds | |
| --- | --- | --- |
| 0 | 322,861 | 320,686 |
| 0.25 | 317,257 | 311,787 |
| 0.5 | 292,662 | 294,743 |
| 1.0 | 243,187 | 250,887 |
| 2.0 | 183,637 | 156,580 |
| 2.9 | 161,596 | 152,953 |
| 5.9 | 90,130 | 97,405 |
| 14.9 | 29,764 | 42,268 |
| 29.0 | 12,220 | 14,862 |
| 48.0 | 6,909 | 8,043 |

EXAMPLE 4

Immunometric assay of ferritin using chemiluminescence

1. The following reagents were incubated together in the wells of a white microtiter plate for 30 minutes at room temperature:
    100 microliters of a standard solution of ferritin in a 50 mM phosphate buffer, pH 7.4, containing 4% bovine serum albumin, 0.9% sodium chloride and 0.05% hyamine.
    100 microliters of a solution of a rabbit antibody to ferritin coupled to horse radish peroxidase in 50 mM phosphate buffer, pH 7.4, containing 0.9% sodium chloride and 0.1% fatty acid-free bovine serum albumin.
    25 microliters of a suspension of magnetizable latex particles coated with rabbit anti-ferritin serum in 10 mM phosphate buffer, pH 7.6 (containing approximately 0.25 mg particles).

2. After the incubation, the magnetizable particles were washed and suspended in reagent for the chemiluminescent measurement of peroxidase as described in Example 1.

| Ferritin Standard (ng/ml) | Luminescence Units | |
| --- | --- | --- |
| 0 | 42 | 47 |
| 5 | 72 | 99 |
| 15 | 83 | 117 |
| 30 | 124 | 197 |
| 60 | 261 | 332 |
| 200 | 855 | 907 |
| 500 | 1639 | 1651 |
| 1000 | 1690 | 1764 |

EXAMPLE 5

Immunoassay of total thyroxine using fluorescence

1. The following reagents were incubated together in the wells of a black microtiter plate (Dynatech) for 60 minutes at room temperature:
    50 microliters of a standard solution of thyroxine.
    100 microliters of a solution of thyroxine coupled to alkaline phosphatase in phosphate/saline buffer, pH 7.4 containing a binding protein blocking agent.
    100 microliters of a suspension of magnetizable latex particles coated with sheep anti-thyroxine serum (containing approximately 0.25 mg particles) in 50 mM phosphate buffer, pH 7.6 containing 0.15M sodium chloride and 1.0 g/l bovine serum albumin.

2. After the incubation the particles were settled and washed in 200 microliters of 0.2M Tris buffer, pH 9.0, containing 1.0 mM magnesium chloride as described in Example 1.

3. The particles in each well were then resuspended in 200 microliters of 0.2M Tris buffer, pH 9.0, containing from 1.0 mM magnesium chloride and 0.37 mM methylumbelliferyl phosphate. After incubation for 10 minutes at room temperature, the fluorescence generated in each well was measured in a Microfluor (Dynatech).

| Thyroxine Standard (micrograms/100 ml) | Fluorescence Units | |
| --- | --- | --- |
| 0 | 3056 | 3085 |
| 2.3 | 1933 | 1921 |
| 5.8 | 1116 | 1207 |
| 11.8 | 743 | 750 |
| 24.6 | 495 | 481 |

EXAMPLE 6

Immunoassay of unconjugated oestriol using fluorescene

1. The following reagents were incubated together in the wells of a black microtiter plate for 60 minutes at room temperature:
    50 microliters of a standard solution of oestriol in human serum.
    100 microliters of a solution of oestriol coupled to alkaline phosphatase in 20 mM phosphate buffer, pH 7.0, containing 0.15M sodium chloride and 1 g/l gelatin.
    100 microliters of a suspension of magnetizable latex particles coated with rabbit anti-oestriol serum (containing approximately 0.25 mg particles) in 20 mM phosphate buffer, pH 7.0, containing 0.15M sodium chloride.

2. After incubation, the particles were settled and washed as described in Example 5.

3. The particles in each well were resuspended in 200 microliters of 0.2M Tris buffer, pH 9.0, containing 1.0 mM magnesium chloride and 0.37 mM methylumbelliferyl phosphate. After incubation for 20 minutes at room temperature, the fluorescence generated in each well was measured in a Microfluor.

| Oestriol Standard (ng/ml) | Fluorescence Units | |
| --- | --- | --- |
| 0 | 3916 | 3926 |
| 2.8 | 2001 | 1982 |
| 5.7 | 1670 | 1553 |
| 14.5 | 1160 | 1024 |
| 29.0 | 781 | 785 |
| 45.0 | 604 | 606 |

We claim:

1. A method of performing an assay for an analyte in a liquid medium which comprises the steps:
    (a) incubating, in an assay vessel, a sample containing said analyte, together with a first, labelled, reagent which is soluble in said liquid medium and wherein the label of said labelled reagent is a component of a fluorescent or luminescent system, and with a second reagent which is bound to magnetically attractable particles that are insoluble in, but suspendable in, said liquid medium; one of said first and said second reagents being a specific binder for said analyte and the other of said first and said second reagents being able to bind either to said analyte or to said specific binder; whereby said labelled reagent becomes partitioned between said liquid medium and said magnetically attractable particles in a proportion which depends on the concentration of said analyte in said sample;

(b) separating said magnetically attractable particles from said liquid medium and removing said liquid medium from said vessel; and (c) resuspending said magnetically attractable particles in another liquid medium containing any further reagents required to react with the labelled reagent to generate a signal, and observing a signal generated by said labelled reagent bound to said magnetically attractable particles, whereby the concentration of said analyte in said sample may be determined.

2. A method as claimed in claim 1, wherein said assay is performed in each vessel of a planar array of assay vessels in fixed relationship to one another.

3. A method as claimed in claim 2, wherein the array of assay vessels is a microtiter plate.

4. A method as claimed in claim 2, wherein each assay vessel is optically screened from its neighbors.

5. A method as claimed in claim 1, wherein observation of the signal generated by the labelled reagent in step (c) is effected from above or below the assay vessel.

6. A method as claimed in claim 1, wherein the magnetically attractable particles are suspendable in the liquid medium without shaking for a period at least as long as the incubation time of the assay.

7. A method as claimed in claim 1, wherein the magnetically attractable particles attenuate the signal generated by the labelled reagent thereon by not more than 50%.

* * * * *